United States Patent
Pelc et al.

(10) Patent No.: US 11,883,226 B2
(45) Date of Patent: Jan. 30, 2024

(54) FOCAL SPOT SHAPE FOR COMPUTED TOMOGRAPHY

(71) Applicant: The Board of Trustees of the Leland Stanford Junior University, Stanford, CA (US)

(72) Inventors: Norbert J. Pelc, Los Altos, CA (US); Adam S. Wang, Palo Alto, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 354 days.

(21) Appl. No.: 17/499,023

(22) Filed: Oct. 12, 2021

(65) Prior Publication Data

US 2022/0110599 A1    Apr. 14, 2022

Related U.S. Application Data

(60) Provisional application No. 63/090,342, filed on Oct. 12, 2020.

(51) Int. Cl.
*A61B 6/00* (2006.01)
*A61B 6/08* (2006.01)
*G06T 11/00* (2006.01)

(52) U.S. Cl.
CPC ............. *A61B 6/5258* (2013.01); *A61B 6/08* (2013.01); *A61B 6/5205* (2013.01); *G06T 11/006* (2013.01); *G06T 2211/40* (2013.01)

(58) Field of Classification Search
CPC ......... A61B 1/00; A61B 6/032; A61B 6/5205; A61B 6/4021; A61B 6/482; A61B 6/4035; A61B 6/405; A61B 6/4064; H05G 1/30; H05G 1/46; H05G 1/52; H05G 1/38; H05G 2/00; G01N 21/8806; H01J 35/147; H01J 35/153; H01J 2235/086; H01J 2235/1204; H01J 35/064; H01J 35/00; H01J 35/04; H01J 35/14; G06T 11/005; G06T 11/008

See application file for complete search history.

(56) References Cited

U.S. PATENT DOCUMENTS

2007/0196006 A1* 8/2007 Hsieh .................... G06T 11/006
                                                              382/131

OTHER PUBLICATIONS

Riederer, et al., The noise power spectrum in computed X-ray tomography. Phys Med Biol. May 1978; 23(3):446-54.
Baek et al., A new method to combine 3D reconstruction volumes for multiple parallel circular cone beam orbits. Med Phys. Oct. 2010; 37(10):5351-60.

* cited by examiner

*Primary Examiner* — Don K Wong

(57) ABSTRACT

An x-ray apparatus includes an x-ray source capable of producing an x-ray beam with a focal spot having a spatial shape that is selected to pre-amplify predetermined spatial frequencies exceeding half a cutoff frequency as compared to spatial frequencies below half the cutoff frequency; an x-ray detector capable of detecting the x-ray beam; and a processor adapted to reconstruct an image from the detected x-ray beam using a filter that compensates the pre-amplified predetermined spatial frequencies. The spatial shape comprises two or more disconnected regions that preferably have widths less than that of a nominal focal spot, combined widths greater than or equal to that of a nominal focal spot, and are separated by less than three times a width of a nominal focal spot.

11 Claims, 6 Drawing Sheets

FOCAL SPOT SHAPE FOR COMPUTED TOMOGRAPHY

CROSS-REFERENCE TO RELATED APPLICATIONS

This application claims priority from U.S. Provisional Patent Application 63/090,342 filed Oct. 12, 2020, which is incorporated herein by reference.

STATEMENT OF FEDERALLY SPONSORED RESEARCH

None.

FIELD OF THE INVENTION

The present invention relates generally to x-ray computed tomography.

BACKGROUND OF THE INVENTION

Computed tomography (CT) is one of the main medical imaging modalities. It provides fast, volumetric imaging at high spatial resolution. However, spatial resolution is still limited by a number of factors, including the finite size of the x-ray focal spot. While a smaller focal spot could be used to increase spatial resolution, it would reduce the flux of the x-ray tube due to thermal limitations of the anode, resulting in higher noise or longer scan times. This tradeoff has long been one of the fundamental limits to CT spatial resolution and image noise, which often results in increased radiation dose.

SUMMARY OF THE INVENTION

Herein is disclosed a unique method to boost spatial resolution and/or reduce noise in CT imaging, overcoming the problems faced by prior approaches. This method provides an entirely new way to overcome fundamental tradeoffs in CT resolution and noise that is complementary to existing methods. Other (complementary) existing methods focus on improving thermal properties of the anode or on improving resolution/decreasing noise using reconstruction algorithms or image-processing software.

In one aspect, the invention provides an x-ray apparatus comprising: an x-ray source capable of producing an x-ray beam with a focal spot having a spatial shape that is selected to pre-amplify predetermined spatial frequencies exceeding half a cutoff frequency as compared to spatial frequencies below half the cutoff frequency; an x-ray detector capable of detecting the x-ray beam; and a processor adapted to reconstruct an image from the detected x-ray beam using a filter that compensates the pre-amplified predetermined spatial frequencies. The spatial shape comprises two or more disconnected regions. The disconnected regions of the spatial shape of the focal spot preferably have widths less than that of a nominal focal spot, preferably have combined widths greater than or equal to that of a nominal focal spot, and preferably are separated by less than three times a width of a nominal focal spot.

Preferably, the spatial shape is predetermined by an optimization process that minimizes image noise for matched spatial resolution to that of a nominal focal spot. Preferably, the spatial shape is predetermined by an optimization process constrained by total power and peak power density.

The x-ray source may include modified electron beam optics to produce the x-ray beam with the focal spot having the spatial shape. Alternatively, the x-ray source may include separate filaments with electromagnetic focusing that each produce a lobe to produce the x-ray beam with the focal spot having the spatial shape.

Preferably, the filter compensates by applying the inverse of the pre-amplification of the predetermined higher spatial frequencies. In some implementations, the processor may be adapted to reconstruct the image from the detected x-ray beam uses a filtered backprojection reconstruction algorithm with a matching filter applied as an additional filter during the application of a ramp filter and apodization filter.

DETAILED DESCRIPTION OF THE INVENTION

Figure 1A:
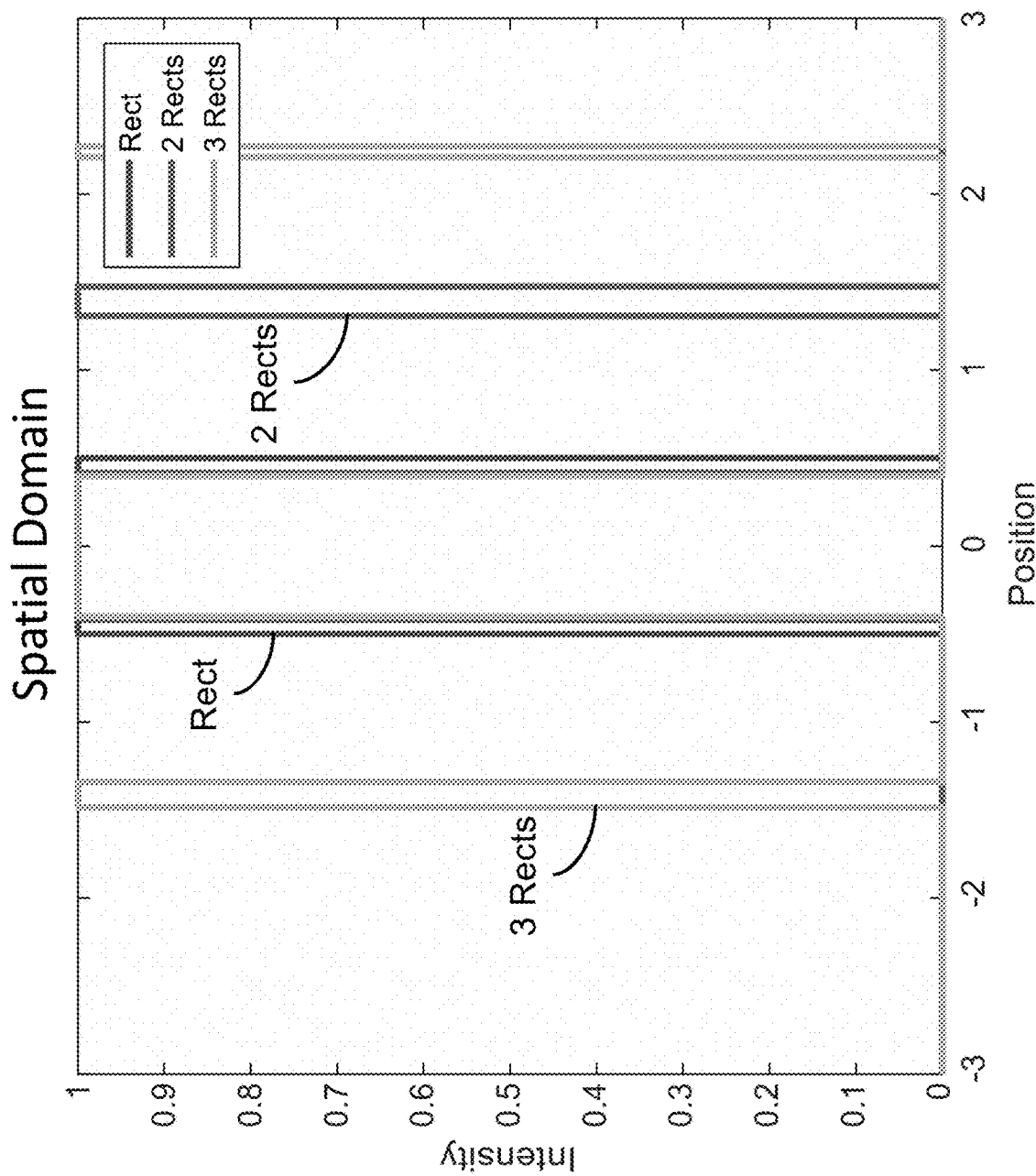
FIG. 1A is a graph of intensity vs. position in the spatial domain showing nominal focal spot (rect) and optimized focal spots for 2 and 3 rects.

X-ray focal spots used in CT imaging are often modeled as Gaussian or rectangular (rect) in shape. A broader focal spot size lowers the spatial resolution of the resulting CT image. At the same time, thermal limitations of the X-ray source anode limit peak power and total power capability of the source. This results in a trade-off between power and spatial resolution, which has impact on all x-ray imaging modalities.

The techniques of the present invention begin with the observation that CT reconstruction methods give unequal weighting to different spatial frequencies for both signal and noise. For example, in the filtered-backprojection reconstruction algorithm, the ramp filter amplifies higher spatial frequencies. While backprojection gives more weight to lower spatial frequencies, this only partly counters the effect of the filter. The net effect is that higher spatial frequencies in the projections are amplified relative to lower spatial frequencies.

A key realization at the basis of the techniques of the present invention is that while signal in the projections is convolved by the focal spot, noise is not and remains white (i.e., relatively equal power at all spatial frequencies) at the detector entrance. Thus, by using the focal spot shape to pre-amplify high-frequency signals (but not noise), the reconstruction does not need to amplify the high-frequency signal (and noise) as much. This results in lower noise for the same signal at higher frequencies in the reconstructed image.

We now provide a more thorough analysis of this approach. Assume the noise in a projection has a frequency amplitude spectrum of N(u) (i.e., a noise power spectrum, NPS, of $|N(u)|^2$) as a function of frequency u. Notably, N(u) does not depend on the focal spot, but rather only on the detector blur and is often assumed to be white (i.e., N(u)= constant). If we ignore cosine weighting (if used) in the reconstruction processing, the noise power spectrum of the projection after filtering with a ramp filter R(u) with cutoff frequency $u_0$ and apodization window G(u) is $$NPS(u)=|N(u)R(u)G(u)|^2.$$

The variance of this filtered projection is the integral of this NPS over all frequencies:

$$\sigma_{Proj}^2 = \int_{-u_0}^{u_0} NPS(u)du.$$

Similarly, the variance of a reconstructed 2D image is approximately proportional to this as well, since backprojection gives a 1/k frequency weighting while the 2D integral over all frequencies (to calculate the image variance) has a k weighting, where k is the magnitude of the 2D spatial frequency.

Let us compare two focal spots with effective shapes (at the detector, i.e. taking into account the magnification of the system geometry) of $f_1(x)$ and $f_2(x)$, and frequency content $F_1(u)$ and $F_2(u)$, respectively. To match their spatial resolution, i.e., match a projection with $f_2$ to that with $f_1$, a matching filter $M(u)=F_1(u)/F_2(u)$ could be applied to projection 2 to compensate for its difference in frequency content. Now that they have matched spatial resolution we can compare their noise. Although they have the same resolution their noise power spectra in their filtered projections will be different:

$$NPS_2(u)=NPS_1(u)|M(u)|^2=|N(u)M(u)R(u)G(u)|^2.$$

Therefore, the relative variance of these filtered projections is $$\int_{-u_0}^{u_0} NPS_2(u)du / \int_{-u_0}^{u_0} NPS_1(u)du \propto \int_{-u_0}^{u_0} |M(u)R(u)|^2 du,$$

assuming the detector noise is white (i.e., N(u)=constant) and no apodization (i.e., G(u)=1).

Therefore, if we wish to minimize noise variance when the spatial resolution is matched to that with focal spot $f_1$, we should find $f_2$ that minimizes an objective function or metric:

$$H(f_2) = \int_{-u_0}^{u_0} \left|\frac{F_1(u)}{F_2(u)} R(u)\right|^2 du.$$

This metric of image noise for matched spatial resolution can be used to guide the choice of focal spot shape, although other metrics or design criteria are possible as well. At the same time, constraints such as total power $P_{total}$, peak power density $PD_{max}$, and the physical constraint that negative electron flux is not attainable (i.e., a non-negative local power constraint) can be imposed:

$$\int f_2(x)dx \leq P_{total},$$

$$0 \leq f_2(x) \leq PD_{max}.$$

Given such a metric and constraints, the focal spot shape can be optimized using optimization methods known to those of skill in the art such as the 'interior-point' algorithm or 'trust-region-reflective' algorithm.

Assuming a nominal focal spot is a rectangular shape (rect), one possible focal spot design is the sum of two or more non-overlapping rect's, where the height, width, and position of the rect's are unknown (until the optimization is conducted) and subject to constraints on height (peak power) and total area (total power). Other focal spot shapes such as Gaussians are possible as well, and the optimal shapes will depend on the performance metric and design constraints. If the results show two or more distinct lobes, the largest one can be considered the main lobe and others as side lobes. The metric described above is invariant to translations ($f_2(x-x_0)$) or flips ($f_2(-x)$), so as a matter of convention, we center $f_2(x)$ on the main lobe and arbitrarily select one flip, recognizing that the other flip has identical performance.

In solving the optimization problem for a sum of rect's subject to a normalized total power ($P_{total}=1$) and normalized peak power density ($PD_{max}=1$), we found that 2 rect's can reduce image noise variance by 53.6% ($H_2=0.4645$) over a conventional single-rect design for matched spatial resolution. With 3 rect's, we reduce variance by 54.4% ($H_3=0.4557$). Increasing the number of rect's does not seem to improve the results further, as shown in the spatial domain graph of FIG. 1A. The optimal solutions for 2 rect's and 3 rect's are $$f_{Opt}^{(2)}(x) = \Pi\left(\frac{x}{0.833}\right) + \Pi\left(\frac{x-1.393}{0.167}\right),$$

$$f_{Opt}^{(3)}(x) = \Pi\left(\frac{x-1.410}{0.142}\right) + \Pi\left(\frac{x}{0.797}\right) + \Pi\left(\frac{x-2.240}{0.061}\right),$$

respectively, where $\Pi$ is a rect of width 1 and height 1 centered at 0:

$$\Pi(x) = \begin{cases} 1, & |x| < .5 \\ 0, & |x| \geq .5 \end{cases}$$

These results suggest using a secondary sidelobe with at least 10% of the total power, although having less than that could still improve the performance of this metric or other metrics or other constraints.

Figure 1B:
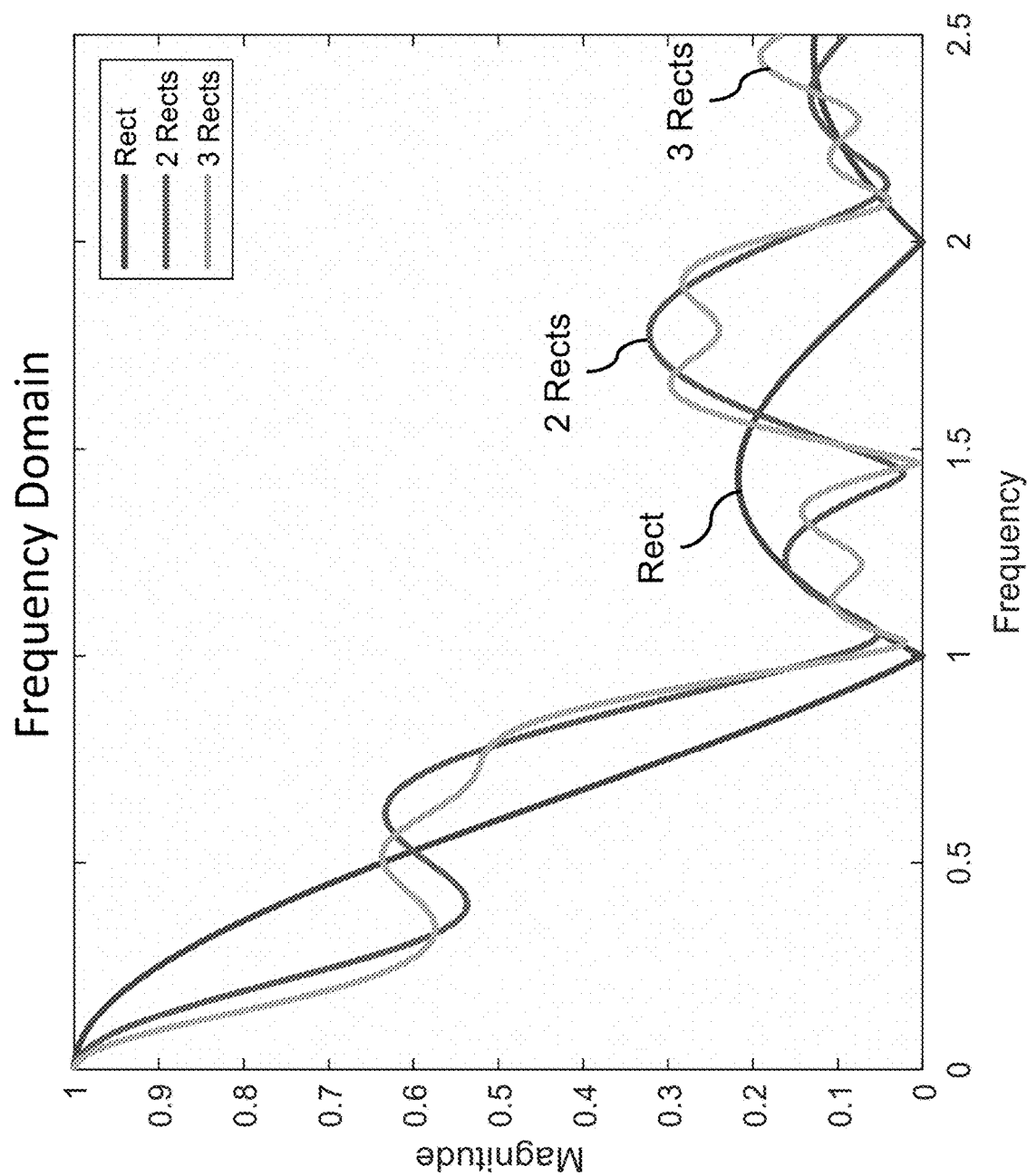
FIG. 1B is a graph of magnitude of Fourier transform in the frequency domain.

In the frequency domain, the optimized focal spots show increased magnitude at higher frequencies (from approximately 0.5 to 1, where these frequencies are normalized to the cutoff frequency), by as much as 0.277 in magnitude, as shown in the Fourier domain graph of FIG. 1B. This can be understood to be caused at least in part by the fact that, for the same total power and peak power, the main lobe of the optimized spot with multiple lobes is narrower than that of the comparison focal spot with a single lobe. The increased magnitude at higher frequencies combined with the increased weighting from the ramp filter in the metric leads to a lower metric, as desired. Although the optimized shapes have lower magnitude at lower frequencies (from 0 to approximately 0.5) by as much as 0.284 in magnitude, the lower weighting from the ramp filter in the metric means the increase in the metric from low frequencies is more than offset by the decrease in the metric from the higher frequencies. The relative importance of different frequencies can also depend on correlations in the noise (i.e., non-white noise) or if apodization is applied. The spatial resolution of these optimized focal spots can be matched to the nominal focal spot by applying the ratio $F_1(u)/F_{opt}(u)$ to projections, in the frequency domain.

The focal spot shape considered in this analysis is in the direction of the filtration step in CT reconstruction, which is generally the focal spot "width" direction, as it is typically defined. The focal spot shape in the "length" direction would remain as that typically used.

The described concept could be extended to arbitrary focal spot shapes and to different metrics of noise and spatial resolution.

To demonstrate the benefit of an optimized focal spot, we performed a simulation of a CT scan of a water phantom (20 cm diameter, with acrylic shell) with 4 steel wires (200 um diameter) at different radial distances. The benefit is greatest when spatial resolution is limited by the focal spot, so we used a nominal focal spot of a 5 mm wide rect for this demonstration study. We compared scans acquired from three different sources: an ideal point source, the rect focal spot, and our optimized focal spot, which has 3 rect's with the same total and peak power as the rect focal spot. A typical system geometry of source-isocenter distance (SID) of 541 mm, source-detector distance (SDD) of 949 mm, and detector pixel size of 1.02 mm was used. The source was subsampled at 100 um intervals (sourcelets), and detector pixels were subsampled at 78 um intervals (detectorlets). The spatial resolution of projections from the optimized spot were matched to that of the rect spot, with the goal of comparing noise. A ramp filter with cutoff frequency at the first zero crossing of the 5 mm rect was used for reconstruction, without any apodization.

Figure 2A:
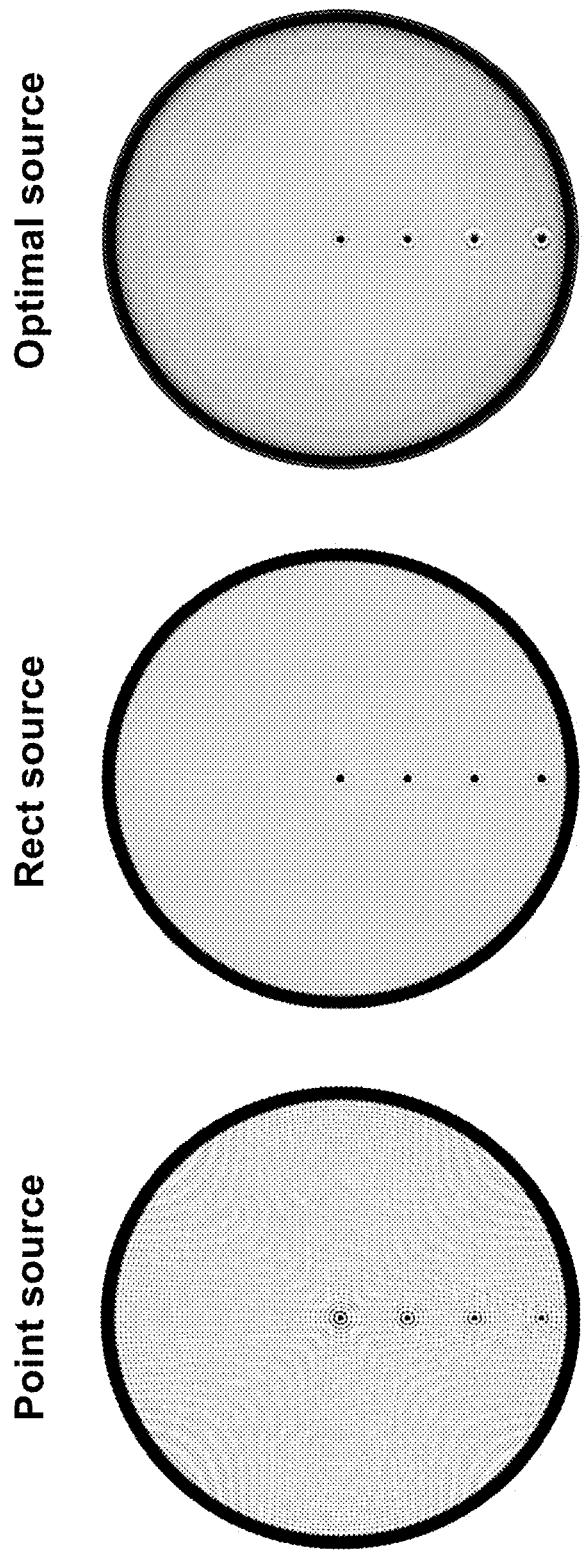
FIG. 2A illustrates images of a noiseless simulation of wires in a water phantom with point, rect, and optimal sources. The images and line profiles show the rect and optimal images have identical spatial resolution.
Figure 2B:
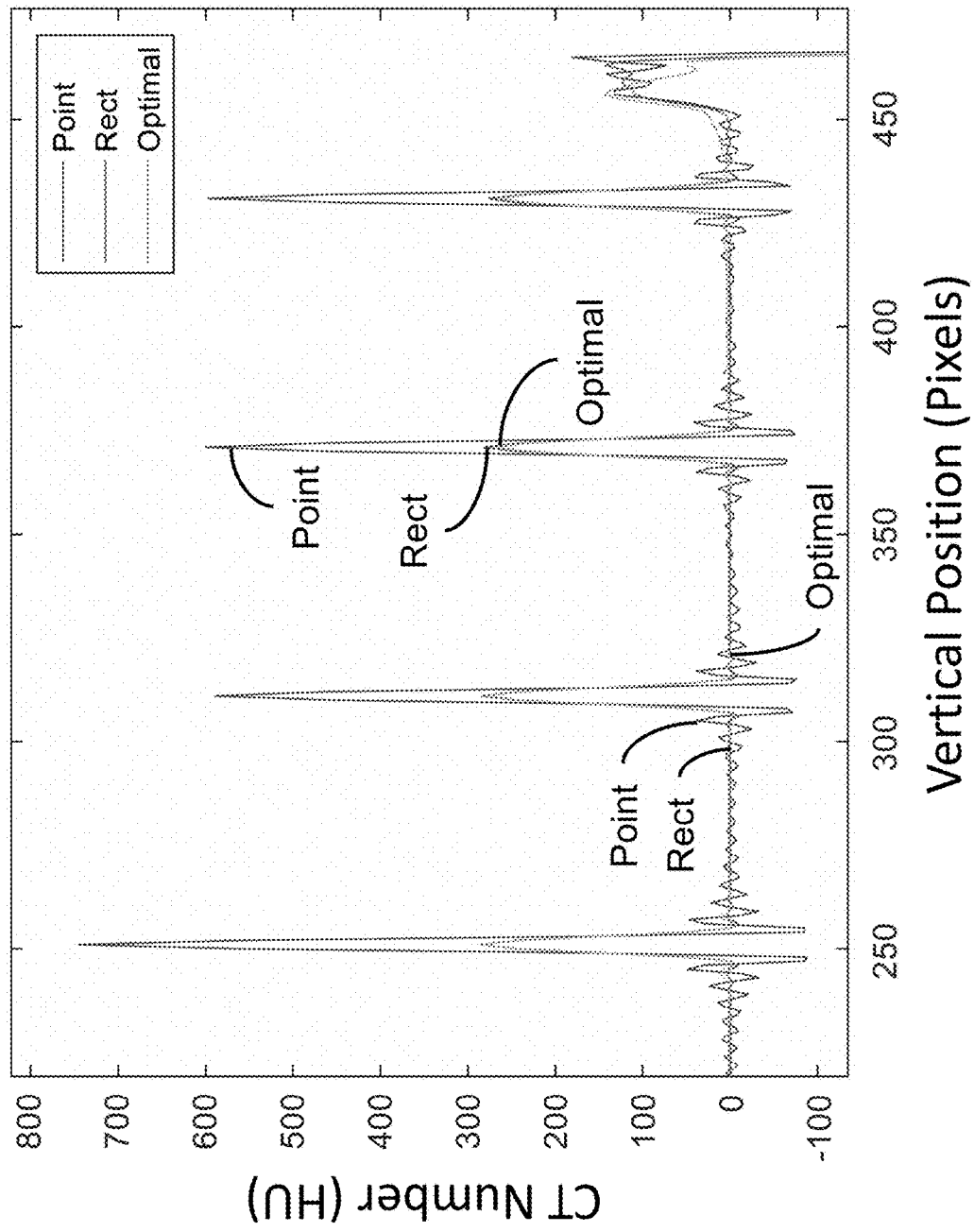
FIG. 2B is a graph showing vertical line profiles of the simulation of FIG. 2A.

FIG. 2A illustrates images of a noiseless simulation of wires in a water phantom with point, rect, and optimal sources. FIG. 2B shows the corresponding line profiles. The images and line profiles show the rect and optimal images have identical spatial resolution. The images from the noiseless simulation show that the point source has the highest spatial resolution, while that of the rect and optimal source are identical after filtering to match their frequency response. This is illustrated by the vertical line profile through the wires, showing the point source has the sharpest peaks, while the rect and optimal sources have the same lower and broader peaks.

Figure 3:
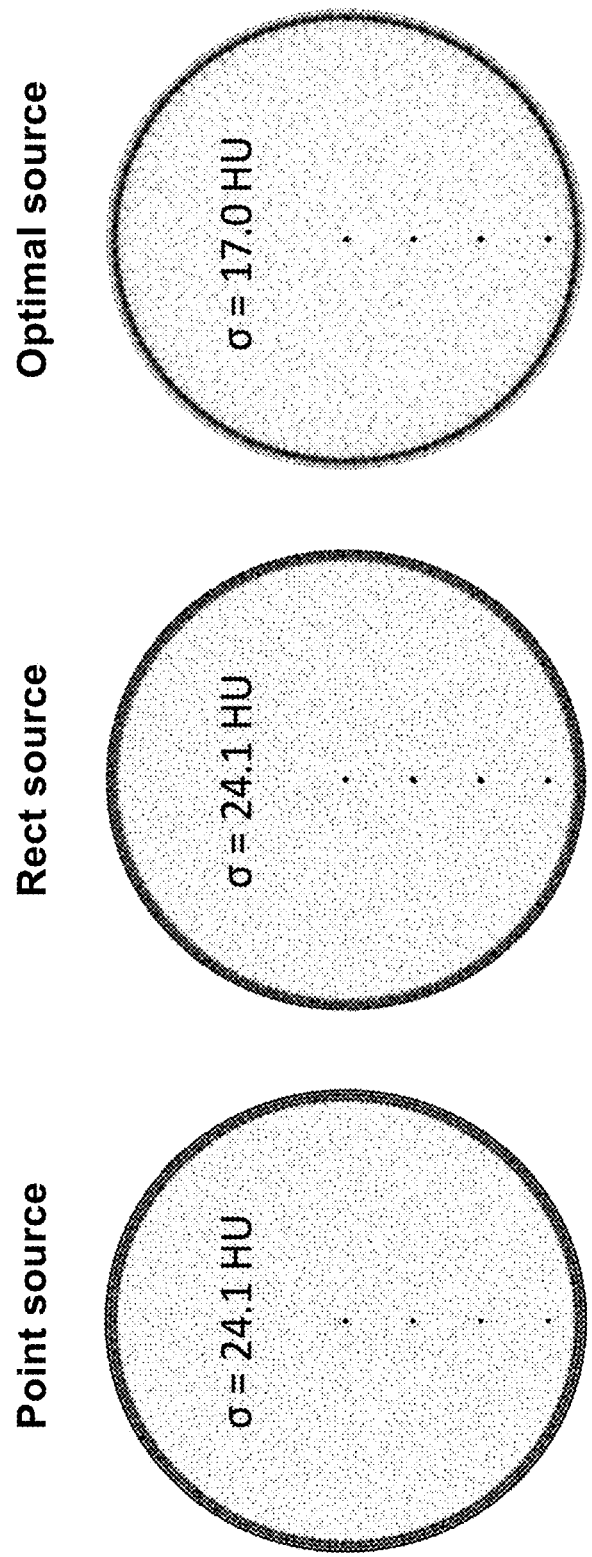
FIG. 3 illustrates a simulation with noisy projections. Noise in the reconstructed images from point and rect sources are identical. Noise from the optimal source is substantially reduced.

FIG. 3 illustrates results from a simulation with noisy projections. Noise in the reconstructed images from point and rect sources are identical. Noise from the optimal source is substantially reduced. When white noise is added to the projections, the reconstructed images have the same spatial resolution as the noiseless case. However, noise in the reconstructed images has different properties, and was determined by 100 independent realizations of noise. The point and rect sources produce identical noise level ($\sigma_{Point}=\sigma_{Rect}=24.1$ HU) and texture since the same ramp filter is applied to white noise. On the other hand, the optimal source has lower noise level ($\sigma_{Opt}=17.0$ HU) and a coarser texture because, for spatial resolution matched to the rect source, noise has been amplified at lower frequencies while it has been reduced at higher frequencies. The net result is a noise level that is 70.5% that of the rect source. This is very close to our noise level prediction of 67.5% ($\sqrt{H_3}=0.675$). This reduction in noise can be used to improve image quality at equal dose, maintain image quality at reduced dose, or something in between. Alternatively, the optimal source can be used to increase spatial resolution at equal noise, match spatial resolution at reduced noise, or something in between.

In this simulation, spatial resolution matching of the optimal source to the rect source was performed in the projections, using the effective source size at isocenter. However, because the effective source size is dependent on the location between the source and the detector, the matching is less accurate away from isocenter. Alternatively, spatial resolution matching could be performed in the reconstructed image domain by locally applying the ratio of modulation transfer functions (MTFs) from the rect and optimal sources to the optimal source images. The spatially-varying MTFs would be accounted for by performing this as a function of image location. The resolution matching can be done using a combination of the two approaches, applying a matching filter tuned to the isocenter (or any other location between the source and detector), and further tuning it locally with spatially dependent filtering.

These techniques can broadly benefit almost all CT scanners since all x-ray sources have thermal limitations and finite size. One major benefit would be in systems or applications that simultaneously require high spatial resolution and high power, such as breast, cardiac, or musculoskeletal imaging. Another major benefit would be in systems that are flux limited, such as those with fixed anodes.

Figure 4:
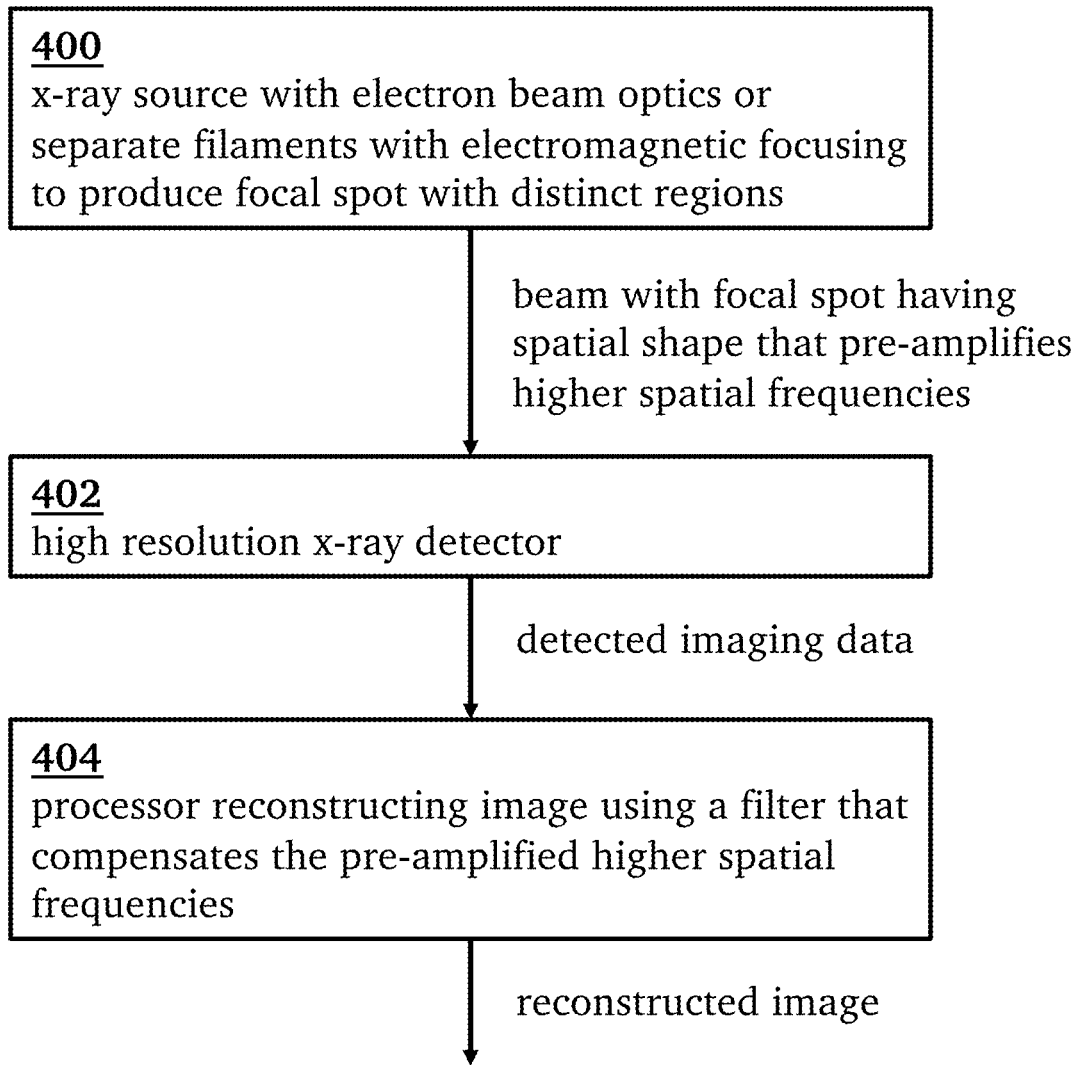
FIG. 4 is a schematic diagram showing a computed tomography apparatus implementing the techniques of the present invention.

FIG. 4 is a schematic diagram showing a computed tomography apparatus implementing the techniques of the present invention. The techniques may be implemented in the form of an x-ray apparatus, such as a CT scanner, having an x-ray source 400 adapted to produce an x-ray beam with a focal spot having a predetermined spatial shape that is selected to pre-amplify predetermined higher spatial frequencies as compared to lower spatial frequencies. The higher spatial frequencies may be those exceeding half the cutoff frequency, while the lower spatial frequencies may be those below half the cutoff frequency.

The x-ray source could produce a focal spot with the predetermined shape by modifying the electron beam optics, or by having separate filaments with electromagnetic focusing that each produce a lobe (main lobe or side lobe).

The x-ray apparatus further includes an x-ray detector 402 capable of detecting the x-ray beam, and a processor adapted to reconstruct an image from the detected x-ray beam using a filter that compensates the pre-amplified predetermined spatial frequencies. Preferably, the x-ray detector would be high enough resolution that the CT image resolution is not limited by the detector. Rather, when the CT image resolution is limited by the x-ray source, our method would have the greatest benefit. Many CT systems have high resolution detectors, including ultra high resolution detectors, flat-panel detectors, and photon counting detectors.

The x-ray apparatus also includes a processor 404 adapted to reconstruct CT images from the imaging data from the detector. Preferably, the reconstruction filter compensates by applying the inverse of the pre-amplification. A conventional filtered backprojection reconstruction algorithm would produce equivalent spatial resolution to the nominal focal spot by applying the matching filter M to projections acquired with the optimized focal spot. The matching filter would be applied as an additional filter during the application of the ramp filter and apodization filter. Similarly, model-based iterative reconstruction or deep-learning image reconstruction methods would incorporate the known optimal focal spot shape into the reconstruction process to benefit from the pre-amplified predetermined spatial frequencies.

Preferably, the x-ray source is adapted to produce a beam with a focal spot whose spatial shape has two or more distinct regions that may be disconnected, e.g., rect regions. The width, amplitude, and location of these regions is determined by the optimization process, which is constrained by total power and peak power density. If the regions are too wide (e.g., wider than the nominal focal spot), the frequency response will be too low at higher frequencies. If the regions are too narrow (e.g., combined width less than that of the nominal focal spot), the total power output will be insufficient. If the regions are too far apart (e.g., more than 3 times the width of the nominal focal spot), their frequency responses will have destructive interference. If the regions are too close, in the limit they merge and become the nominal focal spot.

The invention claimed is:

1. An x-ray apparatus comprising:
an x-ray source capable of producing an x-ray beam with a focal spot having a spatial shape that is selected to pre-amplify predetermined spatial frequencies exceeding half a cutoff frequency as compared to spatial frequencies below half the cutoff frequency;
an x-ray detector capable of detecting the x-ray beam;
a processor adapted to reconstruct an image from the detected x-ray beam using a filter that compensates the pre-amplified predetermined spatial frequencies.

2. The x-ray apparatus of claim 1, wherein the spatial shape comprises two or more disconnected regions.

3. The x-ray apparatus of claim 2, wherein the disconnected regions of the spatial shape of the focal spot have widths less than that of a nominal focal spot.

4. The x-ray apparatus of claim 2, wherein the disconnected regions of the spatial shape of the focal spot have combined widths greater than or equal to that of a nominal focal spot.

5. The x-ray apparatus of claim 2, wherein the disconnected regions of the spatial shape of the focal spot are separated by less than three times a width of a nominal focal spot.

6. The x-ray apparatus of claim 1, wherein the spatial shape is predetermined by an optimization process that minimizes image noise for matched spatial resolution to that of a nominal focal spot.

7. The x-ray apparatus of claim 1, wherein the spatial shape is predetermined by an optimization process constrained by total power and peak power density.

8. The x-ray apparatus of claim 1, wherein the x-ray source comprises modified electron beam optics to produce the x-ray beam with the focal spot having the spatial shape.

9. The x-ray apparatus of claim 1, wherein the x-ray source comprises separate filaments with electromagnetic focusing that each produce a lobe to produce the x-ray beam with the focal spot having the spatial shape.

10. The x-ray apparatus of claim 1, wherein the filter compensates by applying the inverse of the pre-amplification of the predetermined higher spatial frequencies.

11. The x-ray apparatus of claim 1, wherein the processor adapted to reconstruct the image from the detected x-ray beam uses a filtered backprojection reconstruction algorithm with a matching filter applied as an additional filter during the application of a ramp filter and apodization filter.

* * * * *